US00PP09876P

United States Patent [19]

Wain

[11] Patent Number: Plant 9,876

[45] Date of Patent: Apr. 29, 1997

[54] CHRYSANTHEMUM PLANT NAMED 'RUBY LADY'

[75] Inventor: Peter Wain, Hayling Island, United Kingdom

[73] Assignee: Cleangro Ltd., Chichester, United Kingdom

[21] Appl. No.: 629,370

[22] Filed: Apr. 8, 1996

[51] Int. Cl.[6] ..... A01H 5/00

[52] U.S. Cl. ..... Plt./76

[58] Field of Search ..... Plt./76, 81, 82

[56] References Cited

U.S. PATENT DOCUMENTS

| | | | |
|---|---|---|---|
| P.P. 5,777 | 8/1986 | Duffett | Plt./76 |
| P.P. 6,950 | 7/1989 | VandenBerg | Plt./82 |
| P.P. 7,585 | 7/1991 | VandenBerg | Plt./76 |
| P.P. 7,850 | 3/1992 | VandenBerg | Plt./82 |

*Primary Examiner*—Howard J. Locker
*Attorney, Agent, or Firm*—C. A. Whealy

[57] ABSTRACT

A distinct cultivar of Chrysanthemum plant named Ruby Lady, characterized by its flat capitulum form; moderately vigorous and medium growth habit; medium decorative-type inflorescences; dark red purple ray florets; and exceptional postproduction longevity.

1 Drawing Sheet

The present invention relates to a new and distinct cultivar of Chrysanthemum plant, botanically known as *Dendranthema grandiflora* and referred to by the cultivar name Ruby Lady.

The new cultivar is a spontaneous mutation of the commercial cultivar Wain's Pink Lady (U.S. Plant Pat. No. 8,573). The new cultivar was discovered and selected by the inventor in Havant, Hampshire, United Kingdom, as a single plant among a population of plants of the cultivar Wain's Pink Lady. This single plant consistently formed inflorescences having red purple-colored ray florets compared to the pink-colored ray florets of plants of the cultivar Wain's Pink Lady.

Asexual reproduction of the new cultivar by terminal cuttings taken at Havant, Hampshire, United Kingdom, has shown that the unique features of this new Chrysanthemum are stable and reproduced true to type in successive generations.

The following traits have been repeatedly observed and are determined to be the unique characteristics of Ruby Lady. These characteristics in combination distinguish Ruby Lady as a new and distinct cultivar:

1. Flat capitulum form.
2. Moderately vigorous and medium growth habit.
3. Medium decorative-type inflorescences.
4. Dark red purple ray florets.
5. Exceptional postproduction longevity with inflorescences maintaining good substance and color for more than 4 weeks in an interior environment.

The cultivar Ruby Lady has not been observed under all possible environmental conditions. The phenotype may vary somewhat with variations in environment such as temperature, daylength and light intensity, without, however, any variance in genotype.

Plants of the new Chrysanthemum are similar to the mutation parent cultivar Wain's Pink Lady in plant habit and growth rate. However in side-by-side comparisons in Havant, Hampshire, United Kingdom, under commercial practice, plants of the new Chrysanthemum differed from plants of the cultivar Wain's Pink Lady in that the ray floret color of plants of the new Chrysanthemum is red purple whereas the ray floret color of plants of the cultivar Wain's Pink Lady is medium pink.

Plants of the new Chrysanthemum are similar to the cultivar Regal Lady (U.S. Plant patent application Ser. No. 08/316,948, now abandoned) in ray floret color. However in side-by-side comparisons in Oxnard, Calif., under commercial practice, plants of the new Chrysanthemum differed from plants of the cultivar Regal Lady in the following characteristics:

1. Plants of the new Chrysanthemum have smaller and shorter inflorescences than plants of the cultivar Regal Lady.
2. Ray floret color of plants of the new Chrysanthemum is darker red purple than ray floret color of plants of the cultivar Regal Lady.
3. Plants of the new Chrysanthemum have more ray florets but fewer disc florets per inflorescence than plants of the cultivar Regal Lady.

A detailed comparison of plants of the new Chrysanthemum and the cultivar Regal Lady appears in Chart A at the end of the specification.

Plants of the new Chrysanthemum are also similar to the cultivar Cherry Pomona (disclosed in U.S. Plant Pat. No. 7,850) in ray floret color. However, in side-by-side comparisons conducted in Oxnard, Calif., under commercial practice, plants of the new Chrysanthemum differed from plants of the cultivar Cherry Pomona in the following characteristics:

1. Plants of the new Chrysanthemum are taller than plants of the cultivar Cherry Pomona.
2. Inflorescences of plants of the new Chrysanthemum are larger than inflorescences of the cultivar Cherry Pomona.
3. Ray florets of plants of the new Chrysanthemum are longer and broader than ray florets of plants of the cultivar Cherry Pomona.
4. Ray floret color of plants of the new Chrysanthemum is darker red purple than ray floret color of plants of the cultivar Cherry Pomona.
5. Plants of the new Chrysanthemum have more than ray florets per inflorescence than plants of the cultivar Cherry Pomona.
6. Peduncles are more than twice as long on plants of the new Chrysanthemum compared to the peduncles on plants of the cultivar Cherry Pomona.

A detailed comparison of plants of the new Chrysanthemum and the cultivar Cherry Pomona appears in Chart B at the end of the specification.

The accompanying colored photograph illustrates the overall appearance of the new cultivar, showing the colors as true as it is reasonably possible to obtain in colored reproductions of this type. The photograph comprises a top perspective view of a typical flowering 16.5-cm container of Ruby Lady with five cuttings in the container and the terminal inflorescences removed (center-budded pot chrysanthemum). The inflorescence color in the photograph appears lighter than the actual inflorescence color due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18° C., average day temperatures of 30° C., and light levels of 2,000 (cloudy conditions) to 9,000 (sunny conditions) footcandles.

After sticking unrooted cuttings of the new cultivar, plants received 21 long day/short nights followed by short day/long nights until flowering. Three weeks after the start of the short day/long night treatment, plants received three weekly spray applications of daminozide growth retardant at a rate of 2,500 ppm. Measurements and numerical values represent ranges or averages for six typical flowering plants.

Botanical classification: *Dendranthema grandiflora* cultivar Ruby Lady.

Commercial classification: Decorative potted Chrysanthemum.

Parentage: Spontaneous mutation of *Dendranthema grandiflora* cultivar Wain's Pink Lady (U.S. Plant Pat. No. 8,573).

Propagation:

*Type.*—Terminal tip cuttings.

*Time to rooting.*—7 to 10 days with soil temperatures of 21° C.

*Rooting habit.*—Fine, fibrous and well-branched.

Plant description:

*Appearance.*—Perennial herbaceous decorative potted plant. Stems upright, uniform habit and freely branching. Moderately vigorous and medium growth habit.

*Plant height.*—About 30 cm.

*Lateral branch length.*—18.5 to 21 cm.

*Quantity of lateral branches after removal of apical meristem.*—About 4.

*Stem color.*—147B.

*Foliage description.*—Number of leaves per lateral branch: About 16. Leaf arrangement: Alternate. Leaf size, fully expanded: Length: About 8.5 cm. Width: About 4.5 cm. Leaf apex: Acuminate. Leaf base: Attenuate. Leaf margin: Palmately lobed. Leaf texture: Upper and under surfaces slightly pubescent, smooth and dull. Veins prominent on under surface. Petiole length: About 2 cm. Color: Young foliage upper surface: 147A. Young foliage under surface: 147B. Fully expanded foliage upper surface: 147A. Fully expanded foliage under surface: 147B. Venation upper surface: 147B. Venation under surface: 147B. Petiole: 147A.

Flowering description:

*Appearance.*—Decorative inflorescence form. Inflorescences borne on terminals above foliage, arising from leaf axils. Disc and ray florets arranged acropetally on a flat capitulum.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to 2 to 3 weeks of long day/short night conditions after sticking followed by photoinductive short day/long night conditions, flower about 62 to 64 days later.

*Postproduction longevity.*—In an interior environment, inflorescences and foliage of flowering plants will maintain good color and substance for at least 4 weeks in an interior environment.

*Quantity of inflorescences.*—About 7 inflorescences per flowering stem.

*Inflorescence size.*—Diameter: About 9 cm. Depth (height): About 2.6 cm. Diameter of disc: About 3 mm.

*Ray florets.*—Shape: Long, broad. Size: Length: About 4.5 cm. Width: About 1.4 cm. Apex: Rounded. Base: Acute. Margin: Entire. Texture: Satiny, smooth and glabrous. Aspect: Flat. Number of ray florets per inflorescence: About 224. Color: When opening, upper surface: 59B. When opening, under surface: 59B. Mature, upper surface: 59B, fading to 186A with subsequent development. Mature, under surface: 186B.

*Disc florets.*—Shape: Tubular. Size: Length: About 4 mm. Width: About 1 mm. Number of disc florets per inflorescence: About 16. Color: Immature: 154A. Mature: 12A.

*Peduncle.*—Aspect: Strong and angled about 45° to the stem. Length: About 7 cm. Texture: Glabrous. Color: 147B.

*Reproductive organs.*—Androecium: Present on disc florets only. Anther color: 12A. Pollen: Moderate, 12A in color. Gynoecium: Present on both ray and disc florets. Style color: 154A.

Disease resistance: No known Chrysanthemum diseases observed to date on plants grown under commercial greenhouse conditions.

Seed Production: Seed production has not been observed.

CHART A

| CHARACTERISTICS | RUBY LADY | REGAL LADY |
|---|---|---|
| INFLORESCENCE DIAMETER | About 9 cm | About 9.5 cm |
| INFLORESCENCE DEPTH (HEIGHT) | About 2.6 cm | About 33 cm |
| RAY FLORET COLOR, WHEN OPENING, UPPER SIDE | 59B | 70A |
| RAY FLORET COLOR, MATURE, UPPER SIDE | 59B | 70A |
| RAY FLORET COLOR, MATURE UPPER SIDE | 186B | 70C |
| NUMBER OF RAY FLORETS | About 224 | About 192 |
| NUMBER OF DISC FLORET | About 16 | About 32 |
| DIAMETER OF DISC | About 3 mm | About 7.5 mm |

CHART B

| CHARACTERISTICS | RUBY LADY | CHERRY POMONA |
|---|---|---|
| PLANT HEIGHT | About 30 cm | About 28 cm |
| INFLORESCENCE DIAMETER | About 9 | About 8 cm |
| RAY FLORET LENGTH | About 43 cm | About 4 cm |
| RAY FLORET WIDTH | About 1.4 cm | About 0.8 cm |
| RAY FLORET COLOR, WHEN OPENING, UPPER SIDE | 59B | 70A |
| RAY FLORET COLOR, MATURE, UPPER SIDE | 59B | 70B |
| RAY FLORET COLOR, MATURE, UNDER SIDE | 186B | 70D |
| NUMBER OF RAY FLORETS | About 224 | About 190 |
| PEDUNCLE LENGTH | About 7 cm | About 3 cm |

It is claimed:

1. A new and distinct cultivar of Chrysanthemum plant named Ruby Lady, as illustrated and described.

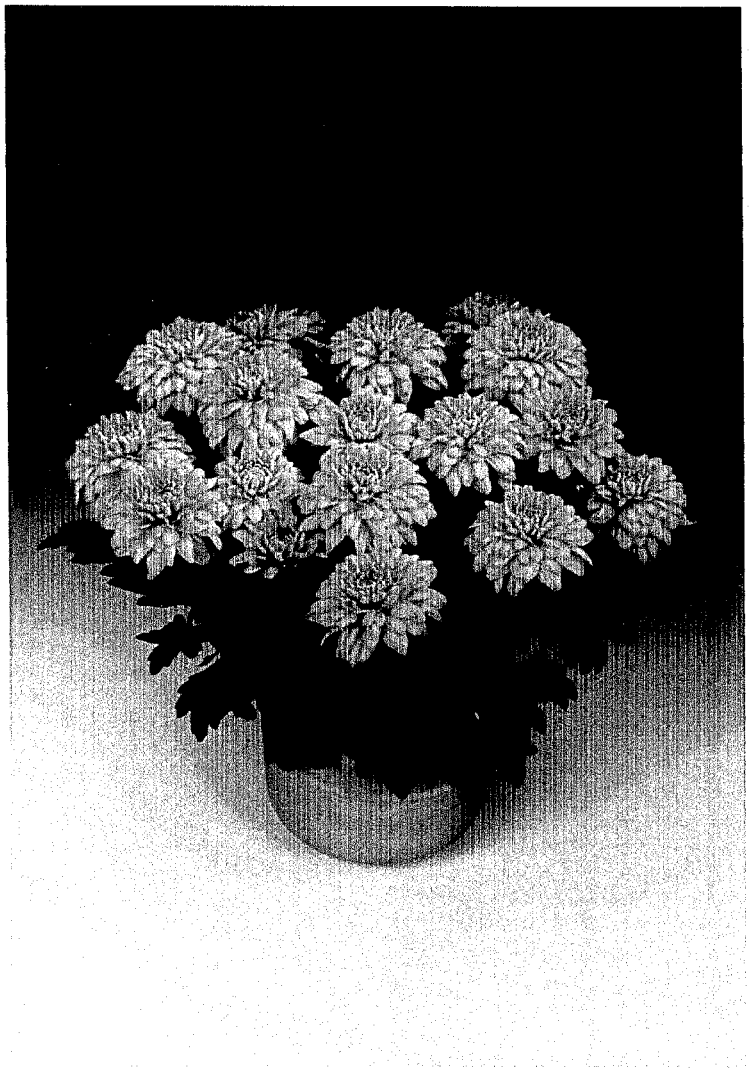

* * * * *